United States Patent
Myers et al.

(10) Patent No.: US 12,322,267 B2
(45) Date of Patent: Jun. 3, 2025

(54) CIRCUITRY AND METHOD

(71) Applicant: Arm Limited, Cambridge (GB)

(72) Inventors: James Edward Myers, Bottisham (GB); Emre Özer, Buckden (GB); Remy Pottier, Grenoble (FR); Jedrzej Kufel, Littleport (GB); John Philip Biggs, Cambridge (GB)

(73) Assignee: Arm Limited, Cambridge (GB)

( * ) Notice: Subject to any disclaimer, the term of this patent is extended or adjusted under 35 U.S.C. 154(b) by 151 days.

(21) Appl. No.: 17/398,198

(22) Filed: Aug. 10, 2021

(65) Prior Publication Data
US 2023/0051410 A1    Feb. 16, 2023

(51) Int. Cl.
G08B 21/18 (2006.01)
G08B 5/36 (2006.01)

(52) U.S. Cl.
CPC ............ G08B 21/18 (2013.01); G08B 5/36 (2013.01)

(58) Field of Classification Search
CPC ................................ G08B 21/24; G08B 21/22
See application file for complete search history.

(56) References Cited

U.S. PATENT DOCUMENTS

| | | | | |
|---|---|---|---|---|
| 3,817,623 A * | 6/1974 | Fruengel | ............... | G01N 21/538 356/442 |
| 4,569,695 A * | 2/1986 | Yamashita | ........ | H01L 21/67051 134/28 |
| 5,659,423 A * | 8/1997 | Schierbeek | ........... | B60R 1/0602 359/603 |
| 7,028,912 B1 * | 4/2006 | Rosen | ................ | G05D 23/1905 236/94 |
| 11,116,381 B2 * | 9/2021 | Strahle | ...................... | G08B 5/32 |
| 11,615,694 B2 * | 3/2023 | Kelly | ................... | G08B 21/245 340/540 |
| 2004/0075640 A1 * | 4/2004 | Liao | ...................... | G06F 3/0317 345/156 |
| 2005/0068527 A1 * | 3/2005 | Nuspliger | ............... | G01N 21/53 356/338 |
| 2007/0030380 A1 * | 2/2007 | Higuchi | ............ | H01L 27/14687 348/340 |
| 2007/0092673 A1 * | 4/2007 | Bruner | .................... | C11D 7/265 427/331 |
| 2012/0116803 A1 * | 5/2012 | Reid | ....................... | G16H 40/20 705/2 |
| 2012/0206384 A1 * | 8/2012 | Marsden | ................ | G06F 3/023 345/173 |
| 2014/0241571 A1 * | 8/2014 | Bilet | ...................... | G06T 7/0004 382/103 |
| 2014/0266749 A1 * | 9/2014 | Thomas | ..................... | G09F 9/33 340/815.45 |
| 2015/0305480 A1 * | 10/2015 | Brousseau | ............... | B25G 1/00 224/267 |

(Continued)

Primary Examiner — Steven Lim
Assistant Examiner — Son M Tang
(74) Attorney, Agent, or Firm — NIXON & VANDERHYE P.C.

(57) ABSTRACT

Apparatus comprises at least one visual indicator element; at least one detector to detect access to the apparatus consistent with a cleaning operation being applied to a surface of the apparatus; and processing circuitry to control a visual indication state of the at least one visual indicator element in response to a detection by the detector of access to the surface of the apparatus.

16 Claims, 7 Drawing Sheets

(56) References Cited

U.S. PATENT DOCUMENTS

| | | | | |
|---|---|---|---|---|
| 2016/0035456 A1* | 2/2016 | Sauro | ............... | H01B 1/24 |
| | | | | 252/511 |
| 2017/0228577 A1* | 8/2017 | Fourre | ............... | G06V 40/1318 |
| 2017/0273273 A1* | 9/2017 | Chou | ............... | A01K 1/0114 |
| 2019/0001933 A1* | 1/2019 | Dellock | ............... | G06F 3/03547 |
| 2019/0015536 A1* | 1/2019 | Dellock | ............... | A61L 2/10 |
| 2019/0091738 A1* | 3/2019 | Chen | ............... | B60H 1/00742 |
| 2019/0117812 A1* | 4/2019 | Olsen | ............... | A61L 2/26 |
| 2019/0299259 A1* | 10/2019 | Marra | ............... | B08B 13/00 |
| 2019/0321868 A1* | 10/2019 | Emrem | ............... | B08B 7/04 |
| 2019/0354753 A1* | 11/2019 | Worrall | ............... | G06V 40/20 |
| 2020/0088667 A1* | 3/2020 | Passaniti | ............... | G01N 33/007 |
| 2020/0250955 A1* | 8/2020 | Goldfain | ............... | G16H 40/20 |
| 2020/0337162 A1* | 10/2020 | Perkins | ............... | G04G 17/04 |
| 2021/0030909 A1* | 2/2021 | McDonald | ............... | H04W 4/80 |
| 2021/0350689 A1* | 11/2021 | Kelly | ............... | G08B 21/245 |
| 2022/0234545 A1* | 7/2022 | Herse | ............... | B60W 60/00 |
| 2023/0083611 A1* | 3/2023 | Giraud | ............... | B60S 1/566 |
| | | | | 15/4 |
| 2023/0122547 A1* | 4/2023 | Akhbari | ............... | A61B 8/00 |
| | | | | 600/437 |
| 2023/0201890 A1* | 6/2023 | Kuepper | ............... | G01S 17/931 |
| | | | | 134/42 |

\* cited by examiner

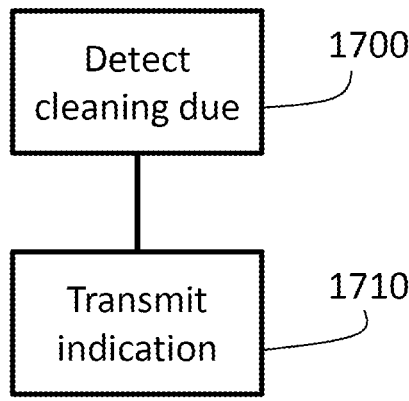 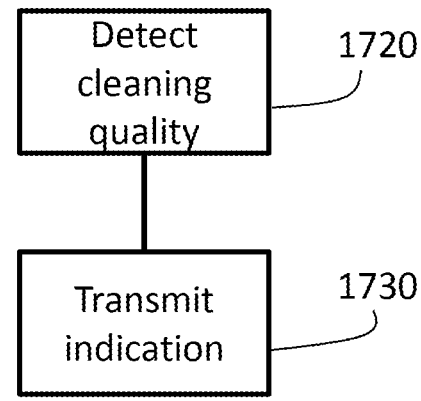
Fig. 17a      Fig. 17b
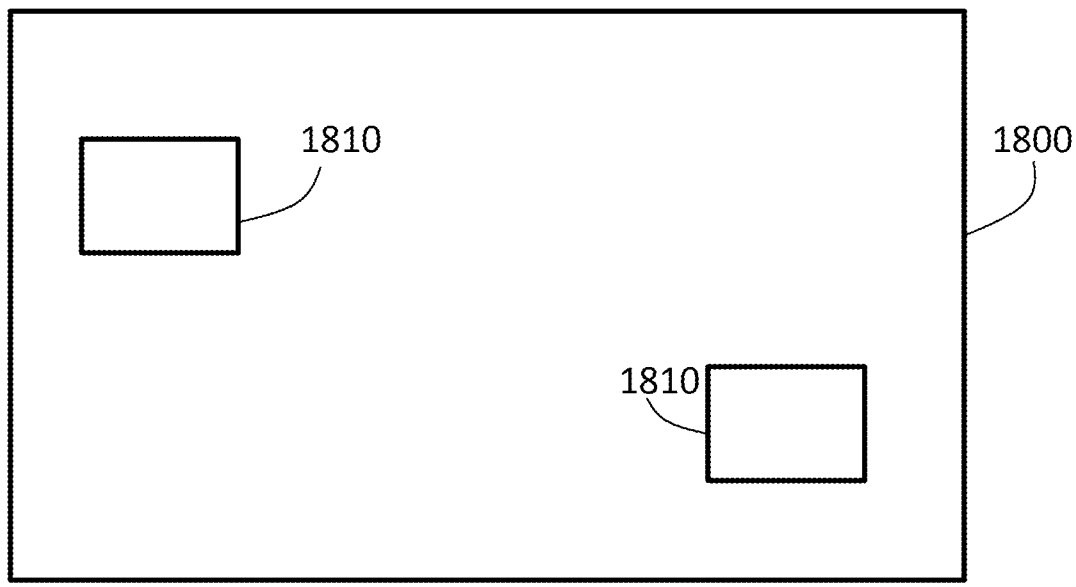
Fig. 18

CIRCUITRY AND METHOD

BACKGROUND

This disclosure relates to circuitry and methods.

Techniques exist for implementing electronic circuitries within or as layers such as flexible layers which can form part of or be applied to an article such as an article of furniture.

SUMMARY

In an example arrangement there is provided apparatus comprising:
  at least one visual indicator element;
  at least one detector to detect access to the apparatus consistent with a cleaning operation being applied to a surface of the apparatus; and
  processing circuitry to control a visual indication state of the at least one visual indicator element in response to a detection by the detector of access to the surface of the apparatus.

In another example there is provided an article of furniture having at least one surface at least partially covered by apparatus comprising:
  at least one visual indicator element;
  at least one detector to detect access to the apparatus consistent with a cleaning operation being applied to a surface of the apparatus; and
  processing circuitry to control a visual indication state of the at least one visual indicator element in response to a detection by the detector of access to the surface of the apparatus.

In another example there is provided a cleaning implement comprising communications circuitry configured to interact with complementary communications circuitry associated with apparatus comprising:
  at least one visual indicator element;
  at least one detector to detect access to the apparatus consistent with a cleaning operation being applied to a surface of the apparatus; and
  processing circuitry to control a visual indication state of the at least one visual indicator element in response to a detection by the detector of access to the surface of the apparatus, in which the at least one detector comprises the complementary communications circuitry configured to interact with the communications circuitry in proximity to the at least one detector.

In another example arrangement there is provided a method comprising:
  detecting access to a substrate, apparatus or the like consistent with a cleaning operation being applied to a surface of the substrate, apparatus or the like; and
  controlling a visual indication state of at least one visual indicator element in response to a detection by the detector of such access to the surface.

Further respective aspects and features of the present technology are defined by the appended claims.

BRIEF DESCRIPTION OF THE DRAWINGS

The present technique will be described further, by way of example only, with reference to embodiments thereof as illustrated in the accompanying drawings, in which:
FIGS. 15, 16, 17a and 17b are schematic flowcharts illustrating respective methods;
FIG. 18 schematically illustrates a cleaning implement.

DESCRIPTION OF EMBODIMENTS

Example Circuitry—Overview

Figure 1:
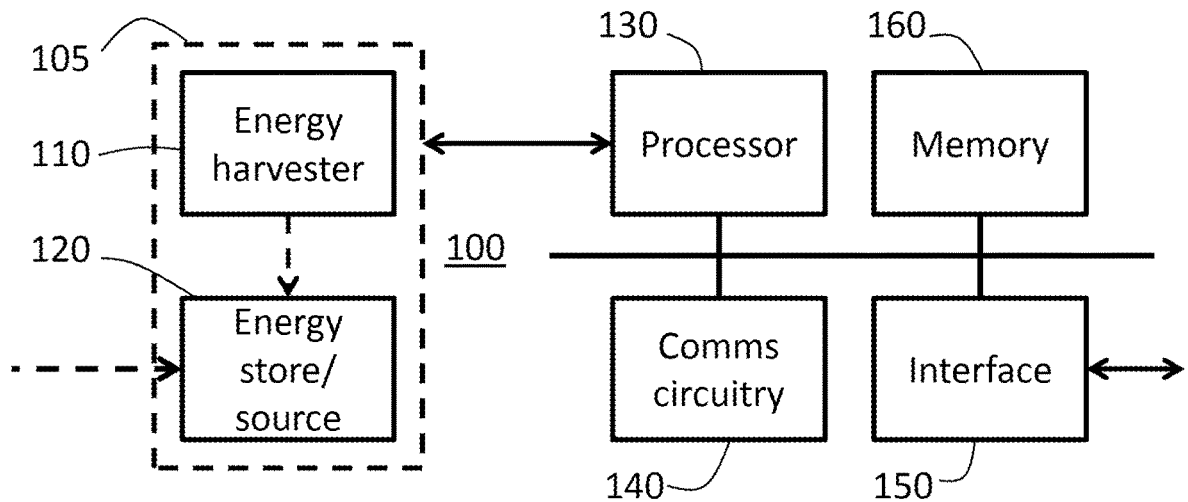
FIG. 1 schematically illustrates example circuitry.

Referring now to the drawings, FIG. 1 schematically represents aspects of an example circuitry 100. This may be implemented by one or more layers such as flexible plastics layers, for example using techniques often referred to as "printed/flexible electronics" in which one or both of conductive tracks and components themselves are implemented by a printing process (such as ink-jet printing or the like) or simpler lithographical process (a low number of masks) onto a flexible substrate.

In the example arrangement of FIG. 1, an energy source 105 provides electrical energy to operate other parts of the circuitry, in particular at least for operations of at least a processing circuitry. In the example drawn, so-called energy "harvesting" is implemented by an energy harvester 110. This term refers to providing electrical energy for the operation of the circuitry 100 from one or more locally available sources, examples including solar, thermal, induction and/or mechanical energy sources. Therefore, the energy harvester 110 may comprise, for example, a solar electrical generator or converter, a thermal electrical generator, for example responsive to a temperature gradient across the energy harvester, and/or induction circuitry to receive electrical energy from a complimentary apparatus placed nearby. These are all just examples of energy harvesting techniques and any one or more of these or other similar techniques may be used. Further examples relating to energy harvesting will be discussed below.

A common feature of energy harvesting arrangements is that the generated power can be relatively low and intermittent, which in turn implies that when that harvested energy is stored, for example by energy storage 120 (for example, capacitive and/or rechargeable battery storage), and used to power the circuitry 100, it is useful that the power consumption of the circuitry, or at least the energy requirement to complete a particular task, is also low.

Of course, the circuitry 100 does not have to use energy harvesting and in some examples they can be powered by mains power, dry cell sources or rechargeable cell sources. The energy source 105 may simply comprise one or more of these, without the use of the energy harvester 110. In other examples the energy harvesting arrangement can be supplemented by mains power, dry cell sources or rechargeable cell sources so as to provide for operation in between energy harvesting events or opportunities.

The circuitry 100 performs processing operations, and in the example of FIG. 1 processing circuitry or processor 130 is provided for this purpose, operating in conjunction with volatile and/or non-volatile memory (shown generically as memory 160). The non-volatile memory provides an example of a non-transitory machine-readable storage medium by which computer software can be stored, the computer software being software which, when executed by the processing circuitry, causes the processing circuitry to perform any of the methods provided by this disclosure.

Similarly, the circuitry may perform communication (via the Internet, a local area network, a point to point link, so-called near-field communications or the like) and to this end communication ("Comms") circuitry 140 is provided as an example of at least one detector comprising communications circuitry configured to interact with complementary communications circuitry (for examples at a cleaning implement) in proximity to the at least one detector. Interface circuitry 150 provides an interface with sensor circuitry, display circuitry or the like (not shown in FIG. 1).

Example Apparatus

Example apparatus will now be described which may embody the circuitry of FIG. 1.

The examples relate to apparatus incorporating measures to potentially improve hygiene by making use of the circuitry of the type described above. The apparatus may be built into an article, such as an article of furniture, for example a table, a table top, a door or a window, or may be embodied as a material layer which may for example include a substrate such as a flexible substrate for mounting to a surface of an article carrying the circuitry of FIG. 1, optionally with an adhesive layer to allow the material layer to be (as a way of mounting to) adhered to an article such as an article of furniture.

Figure 3:
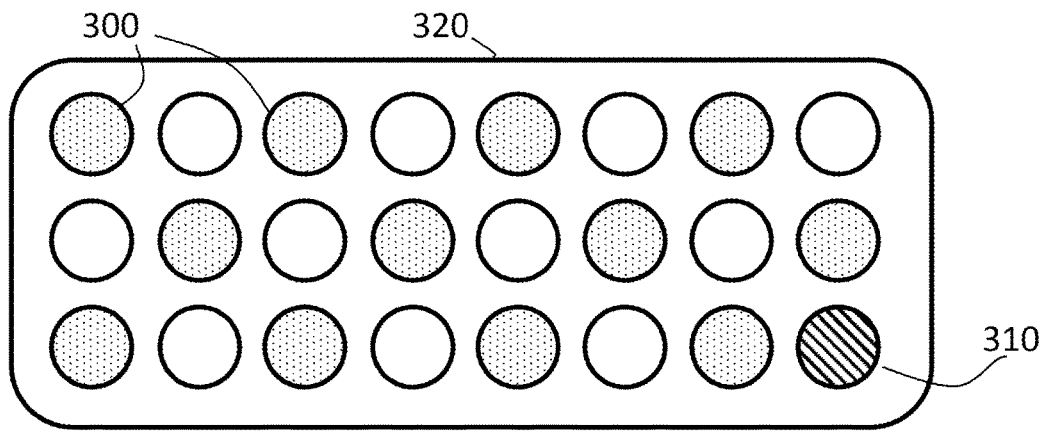
FIGS. 3 and 4 schematically illustrate in plan view examples of an article of furniture to which the apparatus of FIG. 2 is mounted.
Figure 4:
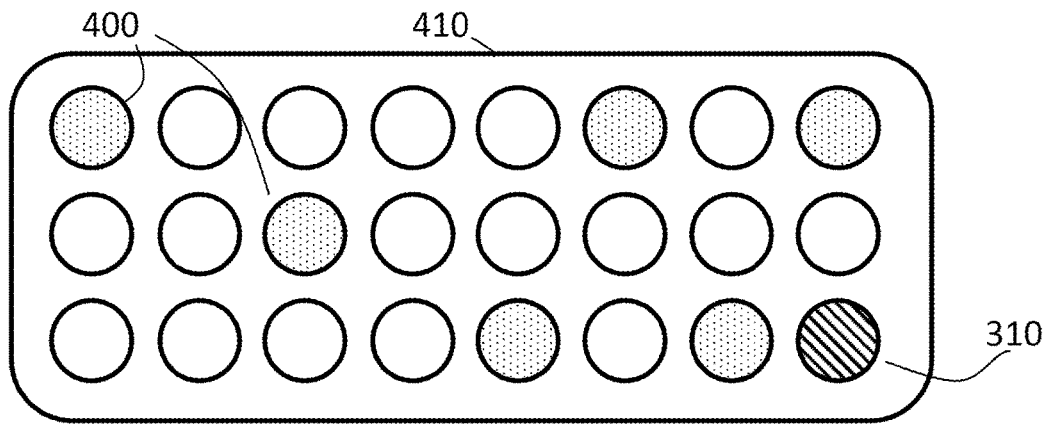
Figure 5:
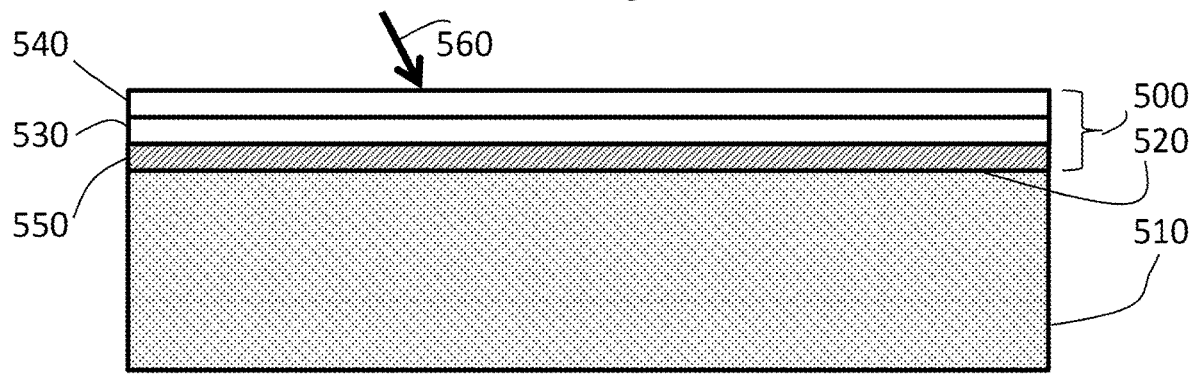
FIG. 5 schematically illustrates a part of the article of furniture of FIGS. 3 and 4 in cross-sectional view.

Therefore, the apparatus may comprise one or both of (i) a substantially transparent layer disposed over the substrate; and (ii) an adhesive portion to mount the substrate to the article. In the arrangement of FIGS. 3-5, an article of furniture has at least one surface at least partially covered by such apparatus.

Figure 2:
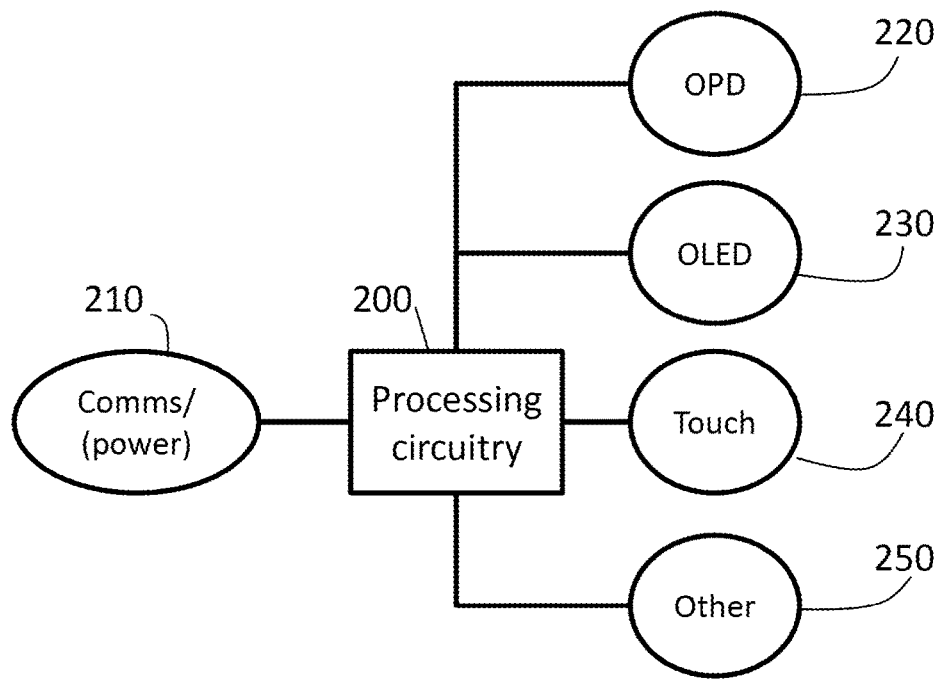
FIG. 2 schematically illustrates an apparatus.

Referring to FIG. 2, processing circuitry 200 incorporates the example functionalities of the processor 130, the memory 160 and the Interface 150 of FIG. 1 and is associated with all connected to circuitry 210 incorporating, for example, the communications circuitry 140 and the energy source 105 of FIG. 1. Via the interface circuitry, the processing circuitry 200 is connected to various devices which may include one or more optical detectors such as organic photodetectors (OPDs) 220, one or more visual indicator elements such as organic light emitting diodes (OLEDs) 230, one or more touch sensors 240 such as capacitive or pressure sensors and one or more other components 250. The components shown in FIG. 2 are just to illustrate the range of options available and particular and further examples will be discussed further below.

Surface Hygiene Monitoring—Overview

As mentioned above, example embodiments can relate to systems for monitoring and potentially improving the hygiene state of a surface such as the surface of an article or the surface of the apparatus itself when applied to or mounted to an article. To this end, the processing circuitry in conjunction with other components to be discussed in various examples below can provide an example of at least one detector configured to detect an instance consistent with a cleaning operation being required.

Using the example components discussed here, embodiments of the disclosure can provide for detecting access to the apparatus, surface or the like consistent with a cleaning operation being applied to that surface, with the processing circuitry 200 providing for the control of a visual indication state of at least one visual indicator element in response to such a detection.

For example, a set of one or more visual indicator elements could be disposed on the surface and arranged to have a particular visual indication state (for example, an illuminated state) when the surface is due for a cleaning operation, for example being detected by the expiry of a timer and/or by an active detection of one or more situations which are indicative of the need for a cleaning operation. Then, in response to detection of access to the apparatus consistent with a cleaning operation, the visual indication state could be changed to another state (for example, a non-illuminated state) as an indication that cleaning has taken place.

This latter indication can be useful to various parties. For example, the person or agent providing the cleaning operation can quickly and easily perceive which articles remain to be cleaned and which have already been cleaned; a supervisor can check that the agent has performed the required cleaning operations; and/or a user of the articles can be reassured that the articles have been cleaned.

The detection of access consistent with a cleaning operation can be made by, for example, one or more touch sensors disposed at the surface, for example in a regular array pattern such as that shown in FIG. 3, where shaded circles 300 indicate, with respect to a schematic plan view of the top 320 of an article such as a table top, potential locations for touch sensors amongst a set or array of candidate locations (the shaded plus the unshaded circles). In this example a visual indicator element 310 is provided on the table top as well. In this example, access consistent with a cleaning operation is detected, at least in part, by a touch detection at each of the touch sensors 300 within a predetermined period such as 20 seconds, for example as may happen when a cloth, sponge or other cleaning implement is moved across the surface during a cleaning operation. The visual indicator element 310 may be arranged to the illuminated when a cleaning operation is required and to be non-illuminated in response to detection of the access consistent with the cleaning operation.

In another example, shown schematically in FIG. 4, the touch sensors 400 are disposed at irregular locations with respect to the article surface 410. Potentially, these locations may be unknown to the person or agent responsible for cleaning the article, which may in turn encourage potentially more thorough cleaning so that the cleaning operation is properly detected within the predetermined time period, given that the person or agent does not know exactly where to clean in order to meet the requirements of the detection.

FIG. 5 schematically illustrates a cross-sectional view of a part of the article shown in plan view in FIGS. 3 and 4 in which the apparatus is embodied as a material layer 500 mounted to an article 510 by an adhesive or similar coating 520. The material layer 500 comprises a substrate 530 carrying at least some of the electronic components discussed above, a substantially transparent protective cover layer 540 and, in this example, and energy harvesting layer 550 such as a layer carrying one or more solar power generation elements. In the case of the use of solar generation, as well as the outer layer 540 being transparent, it is also useful that the substrate 530 is substantially transparent to allow light 560 to reach the solar generation elements.

First Example Apparatus

A first example will be described with reference to FIGS. 6-9. Here, FIG. 6 schematically represents an item which may be carried by a person or agent responsible for performing a cleaning operation, FIG. 7 schematically represents an example of the apparatus, and FIGS. 8 and 9 are schematic flowcharts illustrating respective methods.

Figure 6:
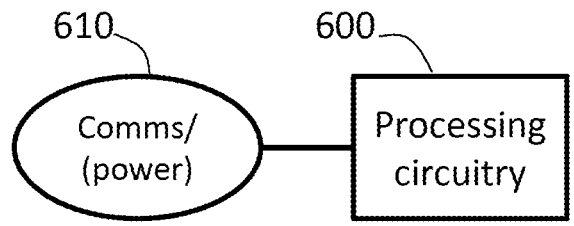
FIG. 6 schematically illustrates an apparatus for carrying by a cleaner.

Referring to FIG. 6, the item to be carried by the personal agent comprises processing circuitry 600 and communications circuitry 610. The item may be embodied as a smartphone or as a cleaning implement for example.

Figure 7:
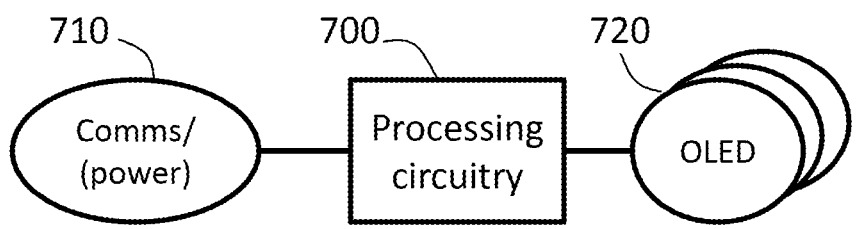
FIG. 7 schematically illustrates an example apparatus.

Referring to FIG. 7, the apparatus comprises processing circuitry 700, communications circuitry 710 and one or more visual indicator elements 720 such as OLEDs.

Figures 8, 9:
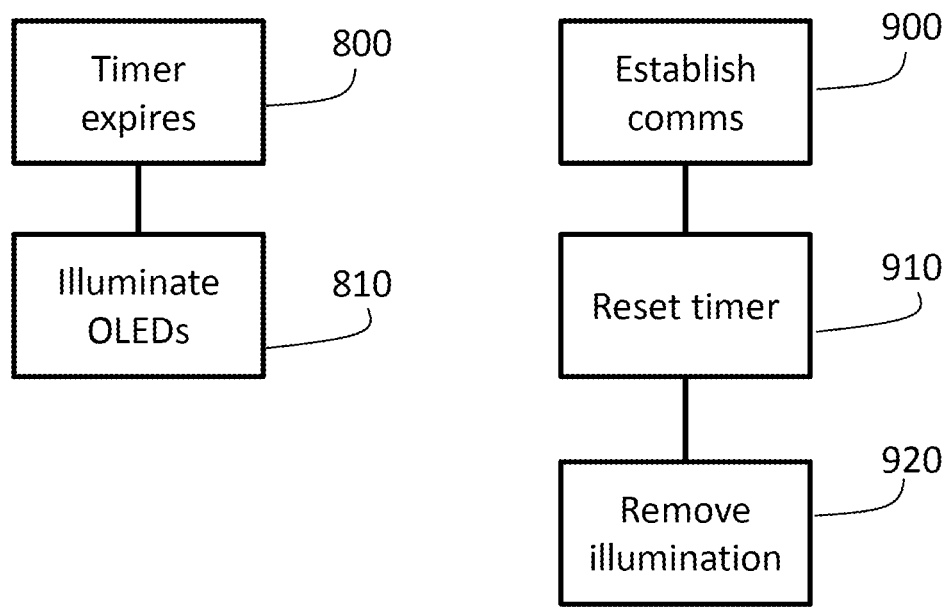
FIGS. 8 and 9 are schematic flowcharts illustrating respective methods.

Referring to FIG. 8, the processing circuitry 700 executes operations to implement a timer such as a countdown timer, having a time period which may be configured for the particular application in use but which may be, for example, one day in a commercial environment or three days in a domestic environment. At a step 800, the processing circuitry detects that the timer expires, which is to say it reaches its terminal count (zero in the case of a countdown timer), in response to which the processing circuitry 700 controls the illumination or at least a change in visual indication state of the one or more visual indicator elements (for example the OLEDs) at a step 810. The result of this processing is that (a) the fact that the apparatus, and therefore in turn the article carrying the apparatus, is ready for or overdue for a cleaning operation, and (b) a visual indication is provided of this ready or overdue status.

Referring to FIG. 9, operations are schematically illustrated by which access consistent with a cleaning operation being applied to the surface of the apparatus may be detected and the visual indication state of the visual indicator elements may be changed. At a step 900, the communications circuitry 710 establishes communication with the communications circuitry 610 of the item carried by the person or agent responsible for cleaning. For example, this may be in the form of so-called near-field or other short range communications so that the establishment of communication implies a physical proximity between the item of FIG. 6 and the apparatus of FIG. 7. In response to this detection at the step 900, which is taken to be indicative of a cleaning operation taking place, the timer is reset by the processing circuitry 700 at a step 910 and, at a step 920, the visual indication state of the one or more visual indicator elements is changed to a state indicative of "not currently requiring a clean", for example by removing the illumination of the OLEDs.

Therefore in these examples, the processing circuitry is configured to control the visual indication state of the at least one visual indicator element in response to an elapsed time since a most recent detection by the at least one detector; and the processing circuitry is configured to control the visual indication state of the at least one visual indicator element in response to detection by the at least one detector of access to the apparatus.

In this example, touch detection of the type described above is not necessarily required; instead, the establishment of communications with the item carried by the personal agent responsible cleaning is taken as sufficient for the detection of an action or access consistent with a cleaning operation being applied.

The item of FIG. 6 may be, for example, a smart phone or the like carried by the person or agent and which is positioned at or near to a predetermined location with respect to the article (such as the location indicated as 310 in FIGS. 3 and 4) while the cleaning operation is taking place.

In other examples, the item of FIG. 6 may in fact be a cleaning implement comprising a communications circuitry (the circuitry 610) configured to interact with complimentary communications circuitry (the circuitry 710) associated with the apparatus to be cleaned. Here, the circuitry 710 may be embodied at a known or (from the point of view of the person or agent) unknown location with respect to the surface to be cleaned, with the result that in order to cause the detection of access consistent with the cleaning operation, the item of FIG. 6 has to be moved across the surface to be cleaned. Optionally, the processing circuitry 700 may implement a delay before the implementation of the step 920 to avoid the person or agent realising where the location of the communications circuitry 710 is positioned.

Second Example Apparatus

In the second and third examples, the at least one detector is also configured to detect an instance consistent with a cleaning operation being required.

In the second example, the detector may comprise a touch detector configured to detect touching of the apparatus, with in some examples a set of two or more touch detectors being spaced apart on the apparatus and respective visual indicator elements associated with the touch detectors, in which the processing circuitry is configured to control the visual indication state of a given visual indicator element in response to a detection by the respective touch detector of touching of the apparatus.

Figure 10:
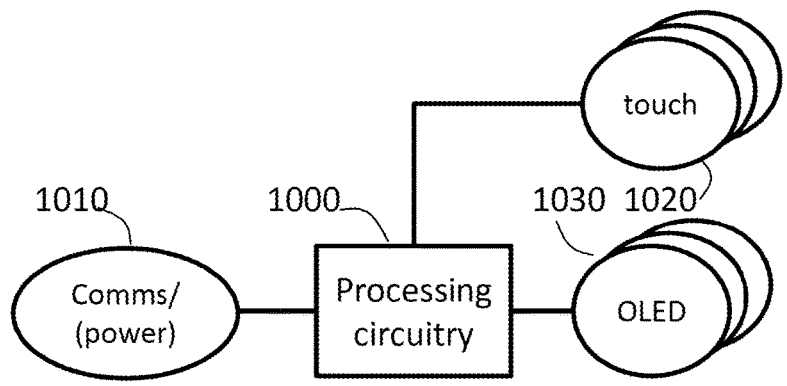
FIG. 10 schematically illustrates an example apparatus.
Figures 11, 12, 13:
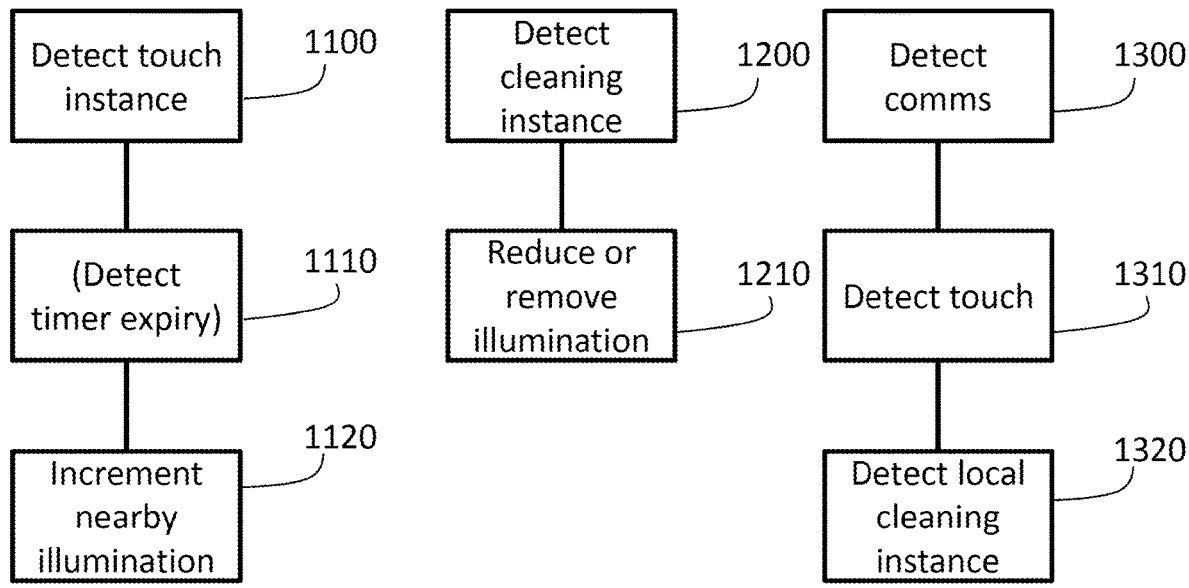
FIGS. 11 to 13 are schematic flowcharts illustrating respective methods.

In this example, FIG. 10 schematically illustrates an example apparatus and FIGS. 11-13 are schematic flowcharts illustrating respective methods.

As discussed generally in the "overview" section above, touch detection may be used to detect access consistent with a cleaning operation. Optionally in addition, touch detection may in fact be used to detect an instance consistent with a cleaning operation being required.

In the example of FIG. 10, processing circuitry 1000 interacts with communications circuitry 1010, one or more touch sensors 1020 and one or more visual indicator elements such as OLEDs 1030.

At an overview level, touch detection may be used to detect that the surface has been touched and therefore that it should be cleaned. This may be combined with the use of a timer as discussed above, for example so that a cleaning operation is deemed to be required if either the surface has been touched in normal use or a time period has expired.

In some examples, a set of two or more touch detectors or sensors 1020 such as capacitive or surface pressure sensors may be provided, for example being spaced apart on the apparatus (for example, at locations which are not necessarily known to either a normal user of the article or to the personal agent responsible for cleaning the article). Respective visual indicator elements such as the OLEDs 1030 may be associated with the touch detectors. For example, this could be a one-to-one association so that each touch detector is associated with a visual indicator element, or there could be another association such as groups of one or more touch sensors being associated with groups of one or more visual indicator elements.

Any of the candidate locations shown schematically in FIGS. 3 and 4 and mentioned above may be populated by touch sensors and/or visual indicator elements.

In the case that this association is provided, it can be useful for the physical location of the visual indicator elements to be at or at least near to the physical location of the respective touch sensors. Of course, in a one-to-one relationship, this could have the effect of revealing the physical locations of the touch sensors, but that is not necessarily the case, particularly in a one-to-many or many-to-many association. The processing circuitry 1000 can be configured to control the visual indication state of a given visual indicator element in response to a detection by the respective touch detector of touching of the apparatus. Specific examples will be described with reference to FIGS. 11-13.

The detection of a touch instance may be a detection that one of the touch sensors has been activated or triggered (that is, by a respective touch) or in other examples that more than one touch sensor has been simultaneously activated or triggered. The activation or triggering may be in response to touching by one finger, or by more than one finger, or by an arm or the like.

Referring to FIG. 11, techniques for making use of touch sensors to provide an indication that a surface or a localised portion of a surface is in need of a cleaning operation may include: at a step 1100, detecting a touch instance at one or more of the touch detectors; and at a step 1120 changing the visual indication state (for example, incrementing illumination) of associated nearby visual indicator elements. Optionally, a further intervening step 1110 can be provided in which, even if no touch is detected during the time period associated with a timer operated by the processing circuitry 1000, the visual indication state can be changed anyway. So, a surface which is touched may need a clean straight away, or a surface which is not touch but which is left for a particular period may be due for a clean in response to expiry of that period.

Note that the detection at the step 1100 can be a transient one, which is to say that the step 1100 is considered to have been executed when a touch instance detection has been made, whether or not that touch is (or those touches are) still present when further steps are executed in response.

Referring to FIG. 12, an access consistent with a cleaning operation can be detected generically at a step 1200 and in response, the visual indication state of the visual indicators can be "reset", for example by reducing or removing illumination in the case of OLEDs, at a step 1210.

The step 1200 can detect an overall cleaning instance applicable to the entire apparatus (for example by the techniques discussed in connection with the step 900 above) or can detect a so-called local cleaning instance applicable to a localised portion of the surface of the apparatus or article. FIG. 13 concerns the detection of a local cleaning instance. In this case, the step 1210 concerns the illumination or visual indication state applicable to visual indicator elements at or close to the location of the detection of the local cleaning instance.

Referring to FIG. 13, at a step 1300 communications are detected with an item such as that shown in FIG. 6, carried by the personal agent responsible for cleaning. At a step 1310 touch is detected by one or more of the touch sensors 1020 while such communications are in operation, which provides for the detection at a step 1320 of a local cleaning instance at the location of the one or more activated touch sensors 1020.

In this way, the touch sensors 1020 provide the functionality of detecting instances which could lead to the surface becoming potentially dirtier or at least in more need of a cleaning operation by detecting touch while the communications with the item of FIG. 6 are not in place, and also provides the functionality of detecting local cleaning instances by similarly detecting touch while the communications are in place.

Third Example Apparatus

Figure 14:
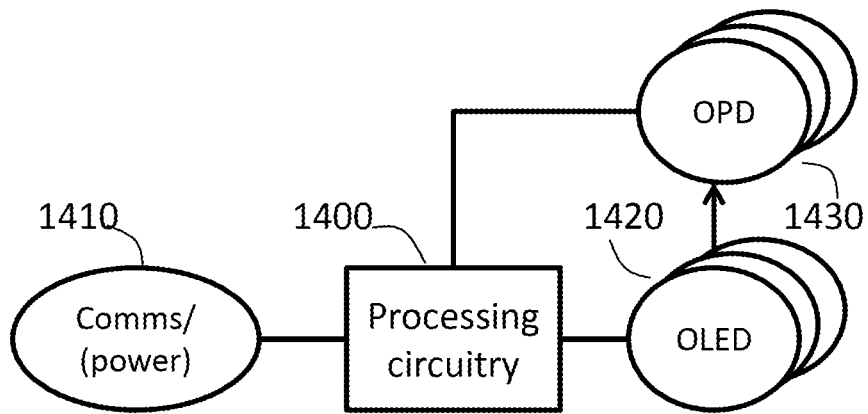
FIG. 14 schematically illustrates an example apparatus.

A third example apparatus is illustrated schematically in FIG. 14 comprising processing circuitry 1400, communications circuitry 1410, one or more light emitting elements 1420 such as OLEDs and one or more optical detectors 1430 such as OPDs.

In these examples, the detector comprises an optical particle detector configured to detect one or more surface particles on the apparatus. As discussed below, a set of two or more optical particle detectors may be spaced apart on the apparatus (for example at any of the candidate locations discussed in connection with FIGS. 3 and 4), with respective visual indicator elements associated with the optical particle detectors; in which the processing circuitry is configured to control the visual indication state of a given visual indicator element in response to a detection by the respective optical particle detector of one or more surface particles on the apparatus.

Note that the reference to detecting "one or more surface particles on the apparatus" implies that the optical particle detector may be capable of and arranged to detect individual particles, or may be triggered by a detection of multiple particles, or may in fact require multiple particles to be present at the same location (or nearby) in order to be triggered. References to detection of a "particle instance" encompass any or all of the possibilities.

The light emitting elements 1420 can provide the visual indication functionality discussed above with reference to the other examples. In addition, however, in conjunction with the optical detectors 1430 they can provide the functionality of an optical particle detector is configured to detect one or more surface particles on the apparatus. For example, while a light emitting element 1420 is illuminated, any dust or other surface particles on the surface of the apparatus or article may cause optical reflection, backscatter or other detectable input to be detected by an optical detector nearby on the surface.

For example, such detections can be distinguished from a mere detection of background or ambient illumination by providing pulsed or intermittent illumination of the light emitting elements and is detecting correlation between the illumination of the light emitting elements and the detection of the reflection, backscatter or other input. To allow the light emitting elements to perform the functionality of the visual indicator elements discussed above in addition to the particle detection functionality discussed here, such intermittent illumination may be primarily "off" but with intermittent short periods of "on" when the light emitting elements are to represent a first visual indication state; or may be primarily "on" but with intermittent short periods of "off" when the light emitting elements are to represent a second visual indication state.

In the same way as discussed above for the touch sensors, a set of two or more such optical particle detectors may be spaced apart on the apparatus and respective visual indicator elements (for example at least some of the light emitting elements 1420 potentially forming part of the optical particle detectors) may be associated with the optical particle detectors.

Figures 15, 16:
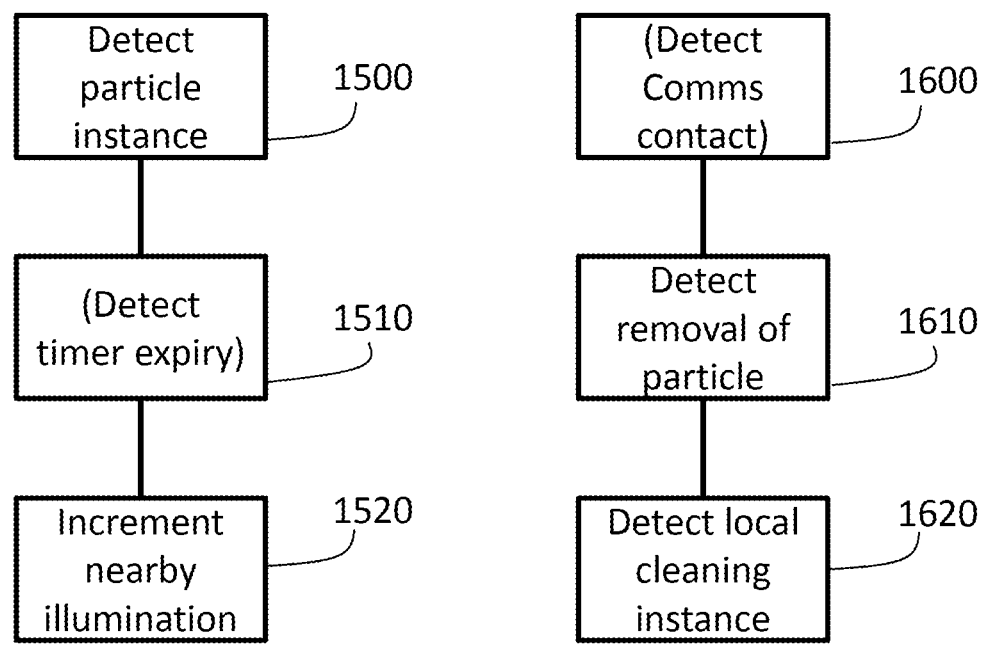
Figure 19:
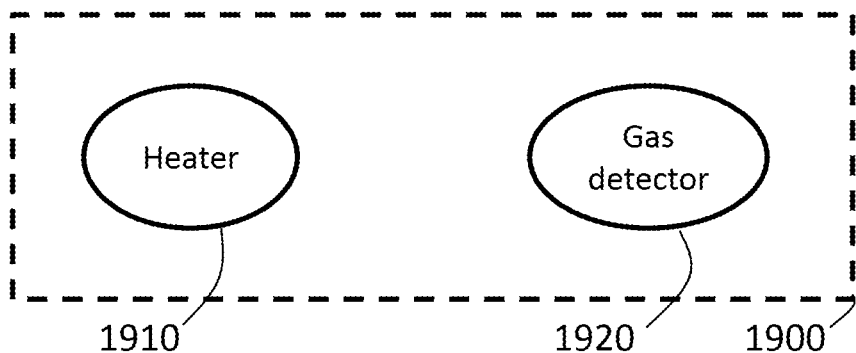
FIG. 19 schematically illustrates a gas detector arrangement.

Referring to FIG. 15, at a step 1500, one or more of the optical particle detectors detects a particle instance at a particular location on the surface and in response, the processing circuitry 1400 causes the illumination of nearby light emitting elements 1420 to be incremented or increased (or more generally for the visual indication state to be changed) at a step 1520. As discussed before, an optional intervening step 1510 may provide for the step 1520 to be triggered by the detection of the expiry of a timer such as a countdown timer so that a surface left for a particular time is deemed dirty even if particles are not in fact detected.

In a similar manner to that discussed in connection with touch sensing, the detection at the step 1500 can be a transient one, which is to say that the step 1500 is considered to have been executed when a particle instance detection has been made, whether or not that particle is (or those particles are) still present when further steps are executed in response.

FIG. 16 refers to the detection of a local cleaning instance. Optionally, the operations of FIG. 16 may be enabled by the detection of a communications link being established at a step 1600, but this is not a requirement given that at a step 1610 the removal of a particle instance is detected, in that an optical particle detector which previously detected the presence of a particle no longer detect the presence of that particle. In response to the removal of that particle instance, a local cleaning instance is detected at a step 1620 and the nearby illumination which was illuminated at the step 1520 can be reduced or removed (or at least the visual indication state changed).

Further Communications Examples

The communications circuitry 1010, as it appears in each of the example embodiments, can also or instead provide for local or wide area communications, for example by a Wi-Fi network, a Bluetooth connection, a mobile communications network or the like. Examples of the use of such arrangements are shown schematically in FIGS. 17a and 17b.

Referring to FIG. 17a, in response to any of the detections discussed above that cleaning is required (for example, timer detections, touch detections, particle detections or the like) at a step 1700, an indication can be transmitted at a step 1710, for example to the smart phone or for example a smart handheld vacuum cleaner of the personal agent responsible to clean the article or for example an autonomous surface cleaning robot responsible to clean the article, that the article requires cleaning.

In another example, referring to FIG. 17b, a detection can be made at a step 1720 of a cleaning quality, for example by detecting whether all of the locations represented by touch detectors have been cleaned by a cleaning operation, and/or detecting whether all of the particles detected by particle detectors have been successfully removed. At a step 1730 such an indication can be transmitted to the person or agent responsible for cleaning and/or to the supervisor of that person or agent.

Therefore, the processing circuitry may be configured to communicate, via the communications circuitry, data indicative of detection of an instance consistent with a cleaning operation being required.

Cleaning Implement Example

FIG. 18 schematically illustrates an example cleaning implement, for example a cloth or sponge or a cleaning robot 1800, carrying flexible circuitry 1810 at one or more locations with respect to the cleaning implement and which embodies the circuitry shown in FIG. 6. By providing the circuitry at more than one location, even if the cleaning implement is folded or used in different orientations, short-range communication with comp entry communications circuitry at the apparatus should still be able to take place.

This therefore provides an example of a cleaning implement comprising communications circuitry configured to interact with complementary communications circuitry associated with the apparatus discussed above.

Gas Detection Example

Instead of or as well as the various detectors discussed above, a dirty apparatus surface or at least a surface deemed to require cleaning can be detected by a gas detector arrangement 1900 comprising a heating element 1910 physically close to a microelectronic gas detector 1920. In use, detection of a dirty surface in place of or in addition to the step 1500, and/or detection of a no-longer-dirty surface in place of or in addition to the step 1610 can be performed by the heating element 1910 briefly heating a local area of the surface, for example for a period of 2 seconds, and the gas detector 1920 detecting emission of one or more gases from the heated area indicative of the presence of contaminants at the heated area. This arrangement requires the gas detected to be in fluid communication with the outer surface of the apparatus, for example by perforations in any protective layer 540.

Such detection arrangements can be provided at multiple spaced apart locations and may have associated nearby visual indicator elements so as to operate in a similar manner to the particle detection embodiments discussed above.

Visual Indicator Element Examples

Figure 20:
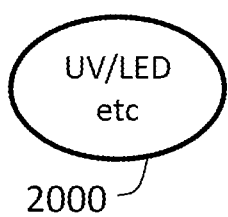
FIG. 20 schematically illustrates a visual indicator element.

Various technologies can be used to provide the visual indicator elements (2000, FIG. 20). In the discussion above, OLEDs were provided as an example of an active element (that is, an element capable of illumination). Other types of LED could also be implemented as examples of active elements. Here, the cleaning status of the surface or a local area of the surface can be indicated by illumination/lack of illumination and/or by variations in colour and/or brightness of illumination.

However, other types of visual indicator element may be used. Examples include visual indicator elements configured to change a current visual indication state in response to a control signal and to retain the current visual indication state in the absence of the control signal. Such elements can use the same technologies, for example, as displays for electronic books. Examples include so-called "electronic paper" or "epaper" elements using technologies such as electrochromic, electrophoretic, electrowetting, electrofluidic or other technologies. Rather than (or in addition to) a transition between "off" and "on", such elements could display different shapes to indicate different visual indication states.

Ultraviolet and Infrared Examples

In other examples, ultraviolet elements such as ultraviolet LEDs, or infrared elements such as infrared LEDs, may be used as the visual indicator elements 2000. These are not necessarily visible to the human eye, but can be provided in addition to visible elements in order to provide for the sanitisation or sterilisation of local areas of the surface of the apparatus or article. To avoid potential optical hazards to nearby human users, activation of the ultraviolet or infrared elements may be restricted to particular periods of the day such as overnight in the case of an office building or the like which is normally unoccupied at that time.

Combination Examples

An example arrangement may have any combination of the sensors, indicators and other features discussed above, for example being disposed at spaced apart locations with respect to the surface.

Energy Harvesting Examples

In the discussion above, an example energy harvesting system was provided by one or more solar power generating elements for example at the layer 550 of FIG. 5.

In other examples, energy harvesting can be performed with respect to the item or apparatus of FIG. 6 when that item is near to the apparatus or article.

In FIG. 6 the device 610 is labelled as "comms/power" and in some examples can—in addition to its communication functions—provide for energy transfer to the apparatus, for example by the apparatus (710, 1010, 1410 or the like) including induction circuitry to receive electrical energy from complementary induction circuitry 610 in proximity to the apparatus.

In other examples, energy harvesting may be implemented by, for example, so-called tribo-electric components at the apparatus, for example at the layer 550, which generate electrical energy by being compressed and released, for example during a cleaning operation, as an example of apparatus configured to generate electrical energy in response to motion relative to the apparatus consistent with performance of a cleaning operation. In fact, such an arrangement can provide the functionality of the detection of access consistent with a cleaning operation, in that the generation of the operational energy itself requires actions consistent with cleaning to have been performed. This would have the further feature that a cursory cleaning operation by the person or agent responsible would not necessarily provide sufficient energy harvesting to power the apparatus, for example in order to change the visual indication state to one indicative of cleaning not being required, or to cause the transmission of a signal (FIG. 17b) indicative of cleaning having been performed adequately.

Example Method

Figure 21:
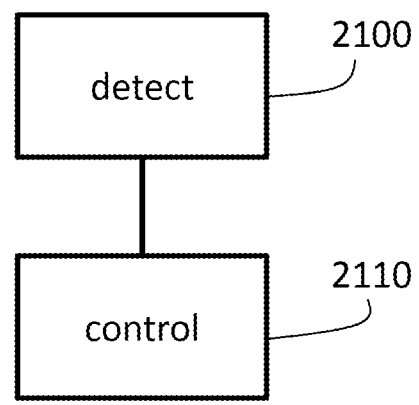
FIG. 21 is a schematic flowchart illustrating a method.

FIG. 21 is a schematically flowchart illustrating a method comprising:
- detecting (at a step 2100) access to a substrate, apparatus or the like consistent with a cleaning operation being applied to a surface of the substrate, apparatus or the like; and
- controlling (at a step 2110) a visual indication state of at least one visual indicator element in response to a detection by the detector of such access to the surface.

The present disclosure also encompasses computer software which, when executed by processing circuitry, causes the processing circuitry to perform such a method. The present disclosure also provides a non-transitory machine-readable medium which stores such computer software.

GENERAL MATTERS

In the present application, the words "configured to . . . " are used to mean that an element of an apparatus has a configuration able to carry out the defined operation. In this context, a "configuration" means an arrangement or manner of interconnection of hardware or software. For example, the apparatus may have dedicated hardware which provides the defined operation, or a processor or other processing device may be programmed to perform the function. "Configured to" does not imply that the apparatus element needs to be changed in any way in order to provide the defined operation.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

The invention claimed is:

1. Apparatus comprising a flexible substrate applied to a surface of the apparatus, the flexible substrate comprising:
   at least one visual indicator element;
   at least one detector configured to detect access to the apparatus consistent with a cleaning operation; and
   processing circuitry configured to control a visual indication state of the at least one visual indicator element in response to a detection by the at least one detector of access to the surface of the apparatus; and
   conductive tracks that connect the processing circuitry to the at least one visual indicator element and the at least one detector;
   wherein the at least one detector is configured to detect an instance consistent with a cleaning operation of the surface being required;
   wherein the at least one detector is disposed at the surface;
   wherein the at least one detector comprises:
      a heater element and a gas detector element, wherein the heater element is configured to heat a local area of the surface, and the gas detector element is configured to detect the instance consistent with the cleaning operation being required in response to detecting emission of one or more gases from the local area heated by the heater element indicative of the presence of contaminants;
   wherein the at least one visual indicator element, at least one detector, processing circuitry, and conductive tracks have been printed onto the flexible substrate.

2. The apparatus of claim 1, in which the at least one detector comprises communications circuitry configured to interact with complementary communications circuitry in proximity to the at least one detector.

3. The apparatus of claim 2, in which:
   the at least one detector is configured to detect an instance consistent with a cleaning operation being required; and
   the processing circuitry is configured to communicate, via the communications circuitry, data indicative of detection of an instance consistent with a cleaning operation being required.

4. The apparatus of claim 1, in which the at least one detector comprises at least one touch detector.

5. The apparatus of claim 1, in which:
   the processing circuitry is configured to control the visual indication state of the at least one visual indicator element in response to an elapsed time since a most recent detection by the at least one detector; and
   the processing circuitry is configured to control the visual indication state of the at least one visual indicator element in response to detection by the at least one detector of access to the apparatus.

6. The apparatus of claim 1, comprising:
   a set of two or more optical particle detectors spaced apart on the apparatus;
   respective visual indicator elements associated with the optical particle detectors;
   in which the processing circuitry is configured to control the visual indication state of a given visual indicator element in response to a detection by the respective optical particle detector of one or more surface particles on the apparatus.

7. The apparatus of claim 1, comprising:
   a set of two or more touch detectors spaced apart on the apparatus;
   respective visual indicator elements associated with the touch detectors;
   in which the processing circuitry is configured to control the visual indication state of a given visual indicator element in response to a detection by the respective touch detector of touching of the apparatus.

8. The apparatus of claim 1, in which the at least one visual indicator element comprises one or more of:
   (i) at least one ultraviolet light emitting element;
   (ii) at least one infrared light emitting element;
   (iii) at least one light emitting element; and
   (iv) at least one visual indicator element configured to change a visual indication state in response to a control signal and to retain a current visual indication state in the absence of the control signal.

9. The apparatus of claim 2, in which the complementary communications circuitry is associated with a cleaning implement.

10. The apparatus of claim 1, in which the apparatus comprises an energy source to provide electrical energy for operations of at least the processing circuitry.

11. The apparatus of claim 10, in which the energy source comprises energy harvesting apparatus, the energy harvesting apparatus comprising one or more selected from the list consisting of:
   (i) induction circuitry to receive electrical energy from complementary induction circuitry in proximity to the apparatus;
   (ii) one or more solar power generating elements; and
   (iii) apparatus configured to generate electrical energy in response to motion relative to the apparatus consistent with performance of a cleaning operation.

12. The apparatus of claim 10, in which the energy source comprises one or both of a mains power source and a battery power source.

13. The apparatus of claim 1, the apparatus comprising a substrate for mounting to a surface of an article.

14. The apparatus of claim 13, comprising one or both of:
   (i) a substantially transparent layer disposed over the substrate; and
   (ii) an adhesive portion to mount the substrate to the article.

15. An article of furniture having at least one surface at least partially covered by apparatus comprising a flexible substrate applied to a surface of the apparatus, the flexible substrate comprising:
   at least one visual indicator element;
   at least one detector configured to detect access to the apparatus consistent with a cleaning operation; and
   processing circuitry configured to control a visual indication state of the at least one visual indicator element in response to a detection by the at least one detector of access to the surface of the apparatus; and
   conductive tracks that connect the processing circuitry to the at least one visual indicator element and the at least one detector;
   wherein the at least one detector is configured to detect an instance consistent with a cleaning operation of the surface being required;
   wherein the at least one detector is disposed at the surface;
   wherein the at least one detector comprises one or more of:
      a heater element and a gas detector element, wherein the heater element is configured to heat a local area of the surface, and the gas detector element is configured to detect the instance consistent with the cleaning operation being required in response to detecting emission of one or more gases from the local area heated by the heater element indicative of the presence of contaminants;
   wherein the at least one visual indicator element, at least one detector, processing circuitry, and conductive tracks have been printed onto the flexible substrate.

16. A cleaning implement comprising communications circuitry configured to interact with complementary communications circuitry associated with apparatus comprising a flexible substrate applied to a surface of the apparatus, the flexible substrate comprising:
   at least one visual indicator element;
   at least one detector configured to detect access to the apparatus consistent with a cleaning operation; and
   processing circuitry configured to control a visual indication state of the at least one visual indicator element in response to a detection by the at least one detector of access to the surface of the apparatus, in which the at least one detector comprises the complementary communications circuitry configured to interact with the communications circuitry in proximity to the at least one detector; and
   conductive tracks that connect the processing circuitry to the at least one visual indicator element and the at least one detector;
   wherein the at least one detector is configured to detect an instance consistent with a cleaning operation of the surface being required;
   wherein the at least one detector is disposed at the surface;
   wherein the at least one detector comprises:
      a heater element and a gas detector element, wherein the heater element is configured to heat a local area of the surface, and the gas detector element is configured to detect the instance consistent with the cleaning operation being required in response to detecting emission of one or more gases from the local area heated by the heater element indicative of the presence of contaminants;
   wherein the at least one visual indicator element, at least one detector, processing circuitry, and conductive tracks have been printed onto the flexible substrate.

* * * * *